(12) United States Patent
Zeitsch

(10) Patent No.: US 6,743,928 B1
(45) Date of Patent: Jun. 1, 2004

(54) PROCESS FOR THE MANUFACTURE OF FURFURAL

(75) Inventor: Karl J. Zeitsch, deceased, late of Kwa Zulu Natal (ZA), by Hanna Tepohl, legal representative

(73) Assignee: International Furan Technology (PTY) Limited, Kwa Zulu Natal (ZA)

( * ) Notice: Subject to any disclaimer, the term of this patent is extended or adjusted under 35 U.S.C. 154(b) by 0 days.

(21) Appl. No.: 09/913,280

(22) PCT Filed: Feb. 11, 2000

(86) PCT No.: PCT/ZA00/00024

§ 371 (c)(1),
(2), (4) Date: Mar. 4, 2002

(87) PCT Pub. No.: WO00/47569

PCT Pub. Date: Aug. 17, 2000

(30) Foreign Application Priority Data

Feb. 11, 1999 (DE) .......................................... 199 05 655

(51) Int. Cl.⁷ ............................................. C07D 307/50
(52) U.S. Cl. ....................................................... 549/489
(58) Field of Search .......................................... 549/489

(56) References Cited

U.S. PATENT DOCUMENTS

| 4,029,515 A | 6/1977 | Kiminki et al. |
| 4,533,743 A | 8/1985 | Medeiros et al. |
| 4,912,237 A | * 3/1990 | Zeitsch ........................ 549/489 |

FOREIGN PATENT DOCUMENTS

| DE | 31 39 188 | 7/1983 |
| DE | 38 42 825 | 7/1989 |
| EP | 0 346 836 | 12/1989 |
| WO | WO 81/00407 | 3/1981 |
| WO | WO 96/25553 | 8/1996 |

* cited by examiner

*Primary Examiner*—Cecilia Tsang
*Assistant Examiner*—Ebenezer Sackey
(74) *Attorney, Agent, or Firm*—Young & Thompson

(57) ABSTRACT

Process for the manufacture of furfural wherein a pentosan-containing raw material acidified or not, is heated to a temperature $T_1$ by admitting steam through valve 2 while the valves 3 and 4 are closed. During the very short heating process, the steam condenses, thus increasing the moisture content of the charge. Then, valve 2 is closed and a leak valve 3 is opened so as to produce a steady small flow of product vapor by gradual depressurization. This causes a slow drop in temperature. When a suitably chosen temperature $T_2$ is reached, the leak valve 3 is closed to terminate the first "gradual depressurization". If at the end of this period no more furfural was obtained, the digestion is completed by opening valve 4 to discharge the residue. If, however, furfural was still obtained, the reactor is reheated and submitted to another "gradual depressurization" period.

10 Claims, 2 Drawing Sheets

PROCESS FOR THE MANUFACTURE OF FURFURAL

This application is a 371 of PCT/2A00/00024 filed on Feb. 11, 2000.

TECHNICAL FIELD OF THE INVENTION

This invention relates to a process for the manufacture of furfural.

BACKGROUND OF THE INVENTION

Chemical reactors must be designed to suit the characteristics of the process intended. In making furfural, this has not been the case. For the first industrial production of furfural, QUAKER OATS used reactors from an abandoned cereal process as they happened to be available, and such reactors leave been used ever since. Later, ROSENLEW and ESCHER WYSS built furfural plants based on reactors designed for making wood pulp. None of the industrial furfural reactors employed today were conceived to meet the special requirements of furfural production, and it is, therefore, not surprising that the yields obtained with these reactors do not even exceed 60%.

The principal yield losses are caused by a reaction between furfural and xylose, so that striving for a high yield forbids having furfural and xylose in the same place. All existing furfural reactors violate this requirement. By pointedly eliminating this deficiency, the process here described permits attaining yields in the order of 100%.

In analytical chemistry, the conversion of pentosan or pentose to furfural is used for a quantitative determination of these substances. This is possible as it was shown that in this procedure the furfural yield is a proven 100%. The procedure consists in an atmospheric digestion of pentosan or pentose in 12% aqueous HCl saturated with NaCl. By contrast, in the present industrial furfural processes mentioned above, a pressure reactor is used to submit the raw material to a steam treatment. By condensing, the steam effects heating to a constant temperature, and by passing through the raw material, it entrains furfural produced therefrom. The furfural reaction is catalysed either by added mineral acid or by various carboxylic acids (mainly acetic acid and formic acid) formed from the raw material. As compared to the analytical furfural process, a fundamental difference lies in the fact that in the latter process an appropriate heat input maintains the reaction medium in a state of boiling, whereas in the industrial processes at any pressure a condensation of steam is thermodynamically incapable of bringing the reaction medium, a pentose solution to boiling, because of the boiling point elevation caused by the xylose. The difference is illustrated schematically in FIG. 1 showing phase diagrams for furfural in an aqueous solution boiling at 110° C. (12% HCl saturated with NaCl), and in an aqueous solution boiling at 101° C. (xylose solution). If a small furfural concentration $\zeta$ is generated in the first system representing the analytical furfural process, this leads to point A lying in the vapour field, which means that any furfural formed in this boiling solution will be instantly transformed to vapour where it cannot react with pentose as the latter is not volatile. Consequently, in this case, loss reactions between furfural and pentose are impossible, which explains the proven yield of 100%.

On the other hand, if a small furfural concentration $\zeta$ is generated in the second system, and if this system is heated by condensing steam at atmospheric pressure, this leads to point B lying in the liquid field. Hence, in the present industrial furfural reactors the reaction medium is not brought to boiling, so that the furfural remaining in solution can react with pentose to form furfural pentose, which explains the known high yield losses. The entrainment of furfural vapour by the steam flow does not change this statement to any significant extent, since this entrainment is a slow and inefficient process giving the loss reactions in the liquid phase plenty of time to take place.

As the principal difference between the analytical furfural process of 100% yield and the industrial processes of less than 60% yield lies in the fact that in the first case the reaction medium is boiling while in the second case it is not boiling, it was compelling to create an industrial process in which the reaction medium is maintained in a state of boiling. In view of the fact that with giant furfural reactors, charged with solids not conductive to being stirred, an indirect energy input by heating the walls can be ruled out, it is the essence of this invention to bring about continuous boiling by a gradual (slow) depressurization. In this fashion, a uniform boiling down to molecular dimensions is enforced without a need for mixing.

Apart from the poor yields achieved, the present commercial processes available are extremely expensive to operate. This is due to the large quantities of steam required, typically 30 to 50 tons of steam per ton of furfural produced, and also the lengthy reaction times of between 2 and 5 hours.

It is therefore an object of this invention to provide a manufacturing process which not only produces a greater yield, but also requires a lower input of steam per ton of furfural produced and results in a shorter reaction time.

DISCLOSURE OF THE INVENTION

According to the invention, a process for the manufacture of furfural includes the steps of charging a reactor with a pentosan containing material, acidified or not, heating the charge by introduction of pressurized steam to a first predetermined temperature, closing the steam inlet valve of the reactor and subjecting the charge to a gradual reduction of pressure until a second predetermined temperature is attained, the depressurization maintaining the liquid phase within the reactor in a constantly boiling state.

In the preferred form the rate of depressurization is sufficient to complete the conversion to furfural before a second predetermined temperature is attained. Also in the preferred form of the invention, the charge is acidified prior to heating.

Also in the preferred form of the invention, the gradual depressurization comprises the controlled leaking of a stream of vapour from the reactor until the second predetermined temperature is attained.

In one form of the invention, a first depressurization is followed by a reheating to a temperature at or near the first predetermined temperature, the reheating being followed by a second gradual depressurization.

Subsequent reheating and depressurization cycles may also be employed if required.

In one form, steam may be added during depressurization to increase the reaction temperature and improve yield.

In the preferred form of the invention, the charge material may be in solid or liquid form. Bagasse from sugar cane is a common feed and may be added to the reactor in solid or slurry form.

Also in the preferred form of the invention the gradual depressurization takes place in the temperature range between 280° Celsius and 150° Celsius, however the preferred range of operation is between 230° Celsius and 170° Celsius.

By an appropriate choice of the first and second temperatures, and by appropriate selection of a mineral or organic acid concentration, it is possible, if desired, to complete the process in a single depressurization period since high temperatures and high acidity result in a short reaction time.

In the preferred form of the invention, phosphoric acid is used as the catalyst.

An apparatus for use in a process according lo the invention comprises a pressure reactor including an inlet for steam under pressure, and an outlet for condensate vapour, the inlet and outlet including one or more valves for controlling the flow rate therethrough.

The outlet includes, after a valve, an orifice plate of predetermined dimensions for assisting in controlling the rate of depressurization. In this form, the valve and orifice plate may be operated in tandem to obtain a range of depressurization rates or a flow control valve governed by temperature or pressure can be used.

In any form of the invention the reactor may be thermally well insulated.

In an alternative form of the invention the reactor walls are designed to be heated. Also in this form, all valve operations are preferably controlled automatically by a computerized control unit. It has been demonstrated experimentally, on a pilot plant scale, that by maintaining the liquid phase of the reaction medium in a state of boiling throughout the reaction period, the furfural yield obtained is substantially greater than current commercial processes, and if correctly controlled may approach yields achieved in the analytical furfural process. The Applicant contends further that apart from increasing the yield, the process of the invention is operable at substantially lowered capital and production costs, for the following reasons:

(1), The process of the invention does not use steam for stripping furfural from the mass of feed material as once the reactor is sufficiently heated, the steam inlet is closed. Further steam will only be required briefly if a reheating cycle is employed.

(2), As a result of the non-use of steam to strip the furfural, the volume of condensate existing the reactor is significantly reduced and the concentration of furfural therein will be proportionately increased in relation to existing processes. This increased furfural concentration will greatly simplify the primary azeotropic distillation. In special cases, for instance in the application of the furfural as a nematicide, no distillation is needed at all.

(3), The product of the invention contains less acetic and formic acid (formed from the raw material) since, after reaching the second predetermined temperature of the decompression, most of these by-products are discharged with the residue. This greatly reduces the loading of the effluent generated by the plant.

DETAILED DESCRIPTION OF THE INVENTION

Figure 1:
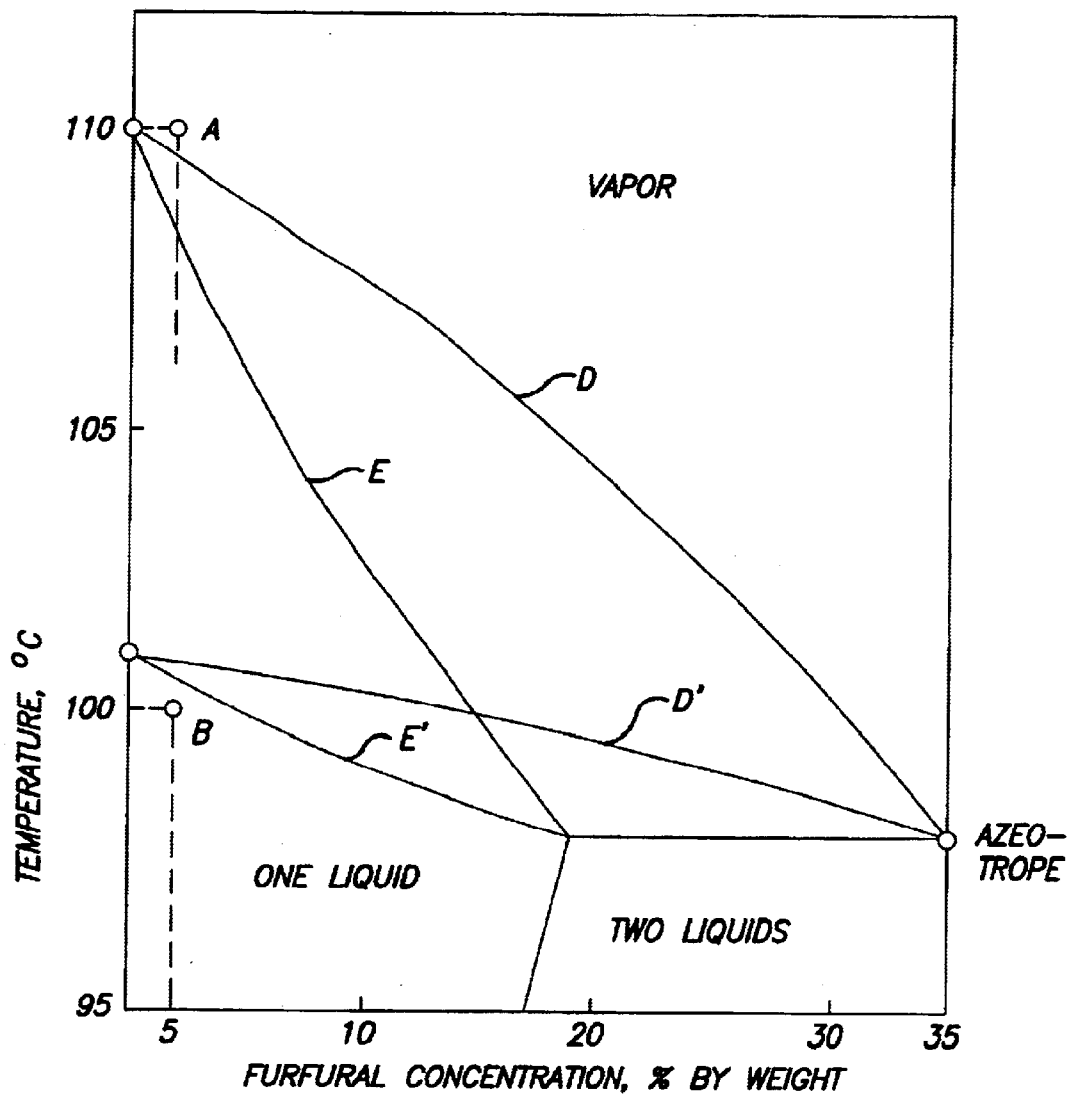
FIG. 1 is a phase diagram depicting the difference between analytical and industrial furfural processes.
Figure 2:
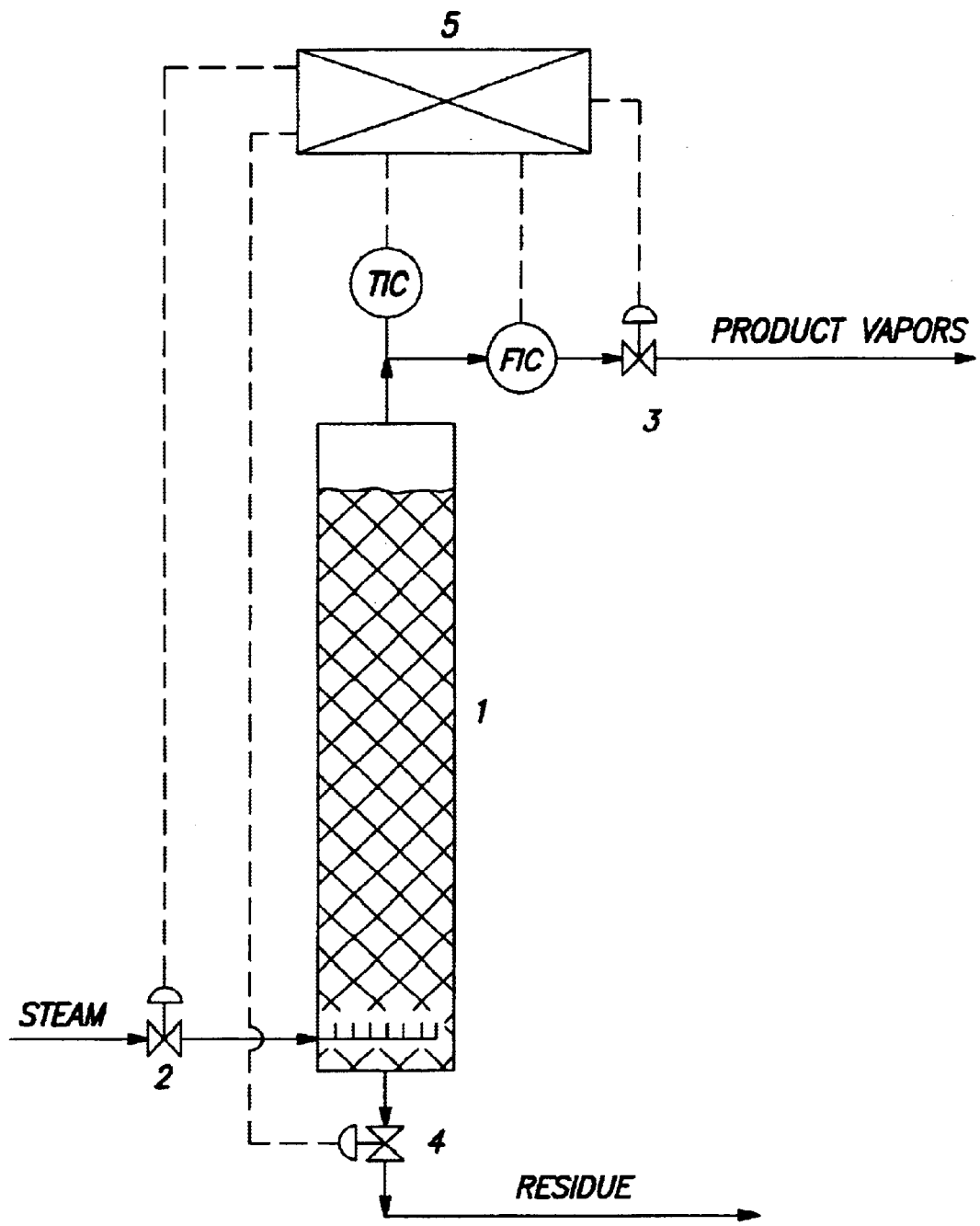
FIG. 2 is a schematic representation of the process and apparatus of the present invention.

The process according to the invention is described below with reference to FIG. 2 which is a schematic diagram of the process and apparatus.

A thermally well insulated reactor 1 charged with raw material acidified or not, is heated to a temperature $T_1$ by admitting steam through valve 2 while the valves 3 and 4 are closed. During the very short heating process, the steam condenses, thus increasing the moisture content of the charge. Then, valve 2 is closed and a leak valve 3 is opened so as to produce a steady small flow of product vapour by gradual depressurization. This causes a slow drop in temperature. When in this fashion a suitably chosen temperature $T_2$ is reached, the leak valve 3 is closed to terminate the first "gradual depressurization". If at the end of this period no more furfural was obtained, the digestion is completed by opening valve 4 to discharge the residue. If, however, furfural was still obtained, the reactor is reheated and submitted to another "gradual depressurization" period. This procedure can be arbitrarily repeated. All valve operations are governed by an automatic control unit 5.

By an appropriate choice of the temperatures $T_1$ and $T_2$, and by an appropriate choice of the acid concentration, it is possible, if desired, to complete the process in a single depressurization period since high temperature and high acidity permit a short reaction time.

Needless to say, designing such an operation is complicated as the furfural reaction takes place over a wide range of temperatures (e.g. from 230° C. to 160° C.), but once calculated, the practical realization of the process is extremely simple.

As due to the continuous leak stream the reaction medium is maintained in a state of boiling throughout the reaction period, the furfural yield corresponds to that of the analytical furfural processes by lying in the order of 100%.

What is claimed is:

1. A process for manufacturing furfural which comprises the steps of:

charging a reactor with pentosan containing material;

heating the charge to a first predetermined temperature by introducing pressurized steam via a steam inlet valve;

closing the steam inlet valve; and subjecting the charge to a gradual depressurization by reducing the pressure in the reactor until a second predetermined temperature is attained; the depressurization being at a rate sufficient to maintain the liquid phase within the reactor in a constantly ebullient state.

2. The process according to claim 1, further comprising the step of acidifying the charge prior to heating.

3. The process according to claim 1, wherein the rate of depressurization is sufficient to complete conversion to furfural before the second predetermined temperature is reached.

4. The process according to claim 1, wherein the complete conversion to furfural is obtained in more than one depressurization from the first predetermined temperature to the second predetermined temperature by the addition of steam.

5. The process according to claim 1, wherein steam is added during the depressurization, for a predetermined period.

6. The process according to claim 1, wherein the gradual depressurization comprises a controlled leaking of a stream of vapor from the reactor until the second predetermined temperature is attained.

7. The process according to claim 1, wherein the gradual depressurization takes place at a temperature range between 280° C. and 150° C.

8. The process according to claim 7, wherein the temperature range is between 230° C., and 170° C.

9. The process according to claim 1, further comprising the step of using phosphoric acid as a catalyst.

10. The process according to claim 1, further comprising the step of adding acetic acid as a catalyst.

* * * * *